United States Patent
Ritter et al.

(10) Patent No.: US 8,431,747 B2
(45) Date of Patent: *Apr. 30, 2013

(54) PROCESS FOR THE PREPARATION OF MONOMERS FOR POLYBENZIMIDAZOLE MATERIALS

(75) Inventors: Joachim C. Ritter, Wilmington, DE (US); Rajiv Dhawan, Wilmington, DE (US)

(73) Assignee: E I du Pont de Nemours and Company, Wilmington, DE (US)

(*) Notice: Subject to any disclaimer, the term of this patent is extended or adjusted under 35 U.S.C. 154(b) by 637 days.

This patent is subject to a terminal disclaimer.

(21) Appl. No.: 12/634,730

(22) Filed: Dec. 10, 2009

(65) Prior Publication Data

US 2010/0160686 A1    Jun. 24, 2010

Related U.S. Application Data

(60) Provisional application No. 61/138,602, filed on Dec. 18, 2008.

(51) Int. Cl.
C07C 209/38 (2006.01)
(52) U.S. Cl.
USPC ............................................. 564/423
(58) Field of Classification Search ............... None
See application file for complete search history.

(56) References Cited

U.S. PATENT DOCUMENTS

| | | | |
|---|---|---|---|
| 3,476,590 A | 11/1969 | Rabilloud et al. | |
| 3,783,137 A | 1/1974 | Gerber | |
| 4,894,458 A | 1/1990 | Masuzawa et al. | |
| 8,163,961 B2 * | 4/2012 | Dhawan et al. | 564/441 |
| 2010/0160596 A1 * | 6/2010 | Dhawan et al. | 528/331 |

FOREIGN PATENT DOCUMENTS

| | | |
|---|---|---|
| EP | 0237955 | 9/1987 |
| JP | 2003292476 | 10/2003 |
| JP | 2005-330470 | 12/2005 |
| JP | 2005330471 | 12/2005 |

OTHER PUBLICATIONS

Knobloch et al., Synthesis of 2.6-Disubstituted Benzo (1.2.4.5) Bisimidazol, Chemische Berichte, 1958, vol. 91, pp. 2562-2565 (Machine Translated).

Cotton and Wilkinson, Advanced Inorganic Chemistry, Periodic Table Only, 1966, Interscience Publishers, $2^{nd}$ Edition, New York.

Boyer et al., The Preparation of 6,7-Disubstituted Quinoxalines, JACS, 1960, vol. 82, pp. 2213-2215.

Blanksma, Nitro Derivatives of 2,6-Dibromotoluene, Chemisch Weekblad, 1913, vol. 9, pp. 968-973, Abstract Only.

* cited by examiner

*Primary Examiner* — Yong Chu
(74) *Attorney, Agent, or Firm* — Kevin S. Dobson

(57) ABSTRACT

A process is provided to produce 2,3,5,6-tetraaminotoluene. Highly pure salts of 2,3,5,6-tetraaminotoluene are produced via reduction of 2,6-diamino-3,5-dinitrotoluene. The 2,3,5,6-tetraaminotoluene salt is precipitated as a clean (>99% purity) product. The salt is a precursor for monomers to make a polybenzimidazole for high performance fibers.

7 Claims, 1 Drawing Sheet

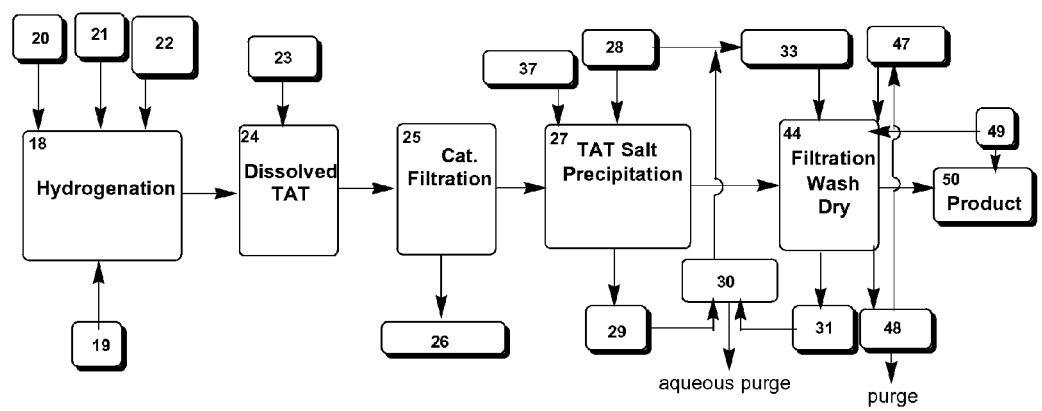

PROCESS FOR THE PREPARATION OF MONOMERS FOR POLYBENZIMIDAZOLE MATERIALS

This application claims priority under 35 U.S.C. §119(e) from, and claims the benefit of, U.S. Provisional Application No. 61/138,602, filed Dec. 18, 2008, which is by this reference incorporated in its entirety as a part hereof for all purposes.

TECHNICAL FIELD

The disclosure relates to methods of making 2,3,5,6-tetraaminotoluene and 2,3,5,6-tetraaminotoluene salts, which are then used in the manufacture of high-performance polybenzimidazole polymers.

BACKGROUND

The synthesis of preferred polybenzimidazole based high performance fibers requires the selective polymerization of 2,3,5,6-tetraaminotoluene ("TAT") with various substituted and unsubstituted aromatic diacids, such as 2,5-dihydroxyterephthalic acid ("DHTA").

TAT has been mentioned in the literature (e.g., U.S. Pat. Nos. 3,476,590 and 3,783,137) as a comonomer in the synthesis of polybenzarenazole polymers. TAT can be used as a crosslinking comonomer using radical induced crosslinking at the methyl group. For example, in Japanese Patent Application 2005-330470A, TAT is used as a crosslinking comonomer in the synthesis of a polybenzimidazole polymer for film applications. However, none of these references discloses a source or synthesis for TAT.

There remains a need for a process for the efficient production of 2,3,5,6-tetraaminotoluene and of high-purity salts of 2,3,5,6-tetraaminotoluene that can be converted to 2,3,5,6-tetraaminotoluene, or to an aromatic diacid complex of 2,3,5,6-tetraaminotoluene, of high enough purity for use in making a high molecular weight polymer material for producing high-performance fibers.

SUMMARY

In one embodiment, this invention provides a process for preparing 2,3,5,6-tetraaminotoluene

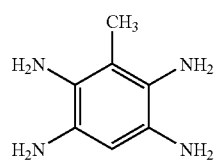

by contacting 2,6-diamino-3,5-dinitrotoluene (II)

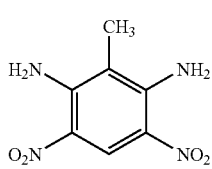

with a hydrogenation catalyst and hydrogen gas, in water in a reaction vessel, to form a reaction mixture, at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraaminotoluene (I); and subsequently filtering the reaction mixture, thereby removing the spent hydrogenation catalyst.

In another embodiment, this invention provides a process for preparing a 2,3,5,6-tetraaminotoluene salt by:
(a) contacting 2,3,5,6-tetraaminotoluene

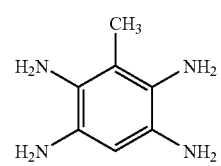

with an aqueous solution comprising 1 to 6 equivalents of acid per mol of 2,3,5,6-tetraaminotoluene, optionally heating the solution, thereby dissolving the 2,3,5,6-tetraaminotoluene;
(b) forming and precipitating the 2,3,5,6-tetraaminotoluene salt by adding an acid to the dissolved 2,3,5,6-tetraaminotoluene; and
(c) washing the 2,3,5,6-tetraaminotoluene salt, wherein all steps are performed under oxygen exclusion.

BRIEF DESCRIPTION OF THE DRAWINGS

The invention is illustrated by way of example and not limited by the accompanying figures.

FIG. 1 is a schematic representation of an embodiment of the process described herein.

DETAILED DESCRIPTION

The following description is exemplary and explanatory only and is not restrictive of the invention, as defined in the appended claims.

A process is provided for preparing a 2,3,5,6-tetraaminotoluene salt comprising the sequential steps under exclusion of oxygen:
a. contacting 2,3,5,6-tetraaminotoluene (I)

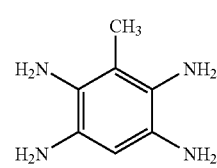

with an aqueous solution comprising 1 to 6 equivalents of acid per mol of 2,3,5,6-tetraaminotoluene, optionally heating the solution, thereby dissolving the 2,3,5,6-tetraaminotoluene;
b. forming and precipitating the 2,3,5,6-tetraaminotoluene salt by adding an acid to the dissolved 2,3,5,6-tetraaminotoluene, and
c. washing the 2,3,5,6-tetraaminotoluene salt,
wherein all steps are performed under oxygen exclusion.
In one embodiment of this process, the process further comprises preparing the 2,3,5,6-tetraaminotoluene for use in step (a) by contacting 2,6-diamino-3,5-dinitrotoluene (II)

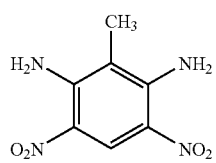

with a hydrogenation catalyst and hydrogen gas, in water in a reaction vessel, to form a reaction mixture, at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraaminotoluene (I); and subsequently filtering the reaction mixture, thereby removing the spent hydrogenation catalyst.

As used herein, the term "TAT salt" or, equivalently, "2,3,5,6-tetraaminotoluene salt," denotes a compound formed by reaction of 2,3,5,6-tetraaminotoluene with an acid such as HCl, acetic acid, $H_2SO_4$, or $H_3PO_4$. One example of a TAT salt is TAT.4HCl.

As used herein, the term "net yield" of a product denotes the actual, in-hand yield, i.e., the theoretical maximum yield minus losses incurred in the course of activities such as isolating, handling, drying, and the like.

As used herein, the term "purity" denotes what percentage of an in-hand, isolated sample is actually the specified substance.

In the process described herein, highly pure salts of 2,3,5,6-tetraaminotoluene ("TAT") are produced from TAT. TAT may be prepared be prepared by hydrogenation of 2,6-diamino-3,5-dinitrotoluene in the presence of a heterogeneous catalyst.

One embodiment of the process described herein which explicitly includes the production of TAT by hydrogenation of 2,6-diamino-3,5-dinitrotoluene is illustrated in FIG. 1; possible minor modifications will be evident to one skilled in the art. The 2,6-diamino-3,5-dinitrotoluene can be made by nitration of 2,6-dichlorotoluene followed by reaction with ammonia. Suitable hydrogenation catalysts comprise metal and/or metal salt; examples include without limitation Pd/C and Pt/C and mixtures thereof, optionally containing other metals from Groups VIII through X such as Fe. The groups are as described in the Periodic Table in *Advanced Inorganic Chemistry* by F. A. Cotton and G. Wilkinson, Interscience New York, 2nd Ed. (1966). Of these catalysts, Pt/C is preferred. The catalyst is typically used in the amount of about 0.5 to about 5.0 wt % metal based on 2,6-diamino-3,5-dinitrotoluene.

An aqueous suspension of 2,6-diamino-3,5-dinitrotoluene, hydrogenation catalyst 22, and water 19 is contacted with hydrogen 21 in the presence of about 0 to about 1 mol equivalent of $NH_{3(g)}$ 20 to form a reaction mixture. With reference to FIG. 1, the hydrogenation is carried out in an aqueous suspension in a reactor 18 at a temperature between about 20 and about 100° C., preferably between about 60° and about 85° C., and a hydrogen pressure of between about 45 and about 500 psi (0.31 to 3.45 MPa), preferably about 300 psi (2.07 MPa), in the presence of about 0 to about 1 mol equivalent of $NH_{3(g)}$ 20. Reaction continues for a time sufficient to consume about 6 to 7 mol equivalents of hydrogen, thereby producing 2,3,5,6-tetraaminotoluene ("TAT"). The time required depends on the details of the specific set up but is typically about 2 hours.

In one embodiment, as shown in FIG. 1, about 1 to about 6 equivalents, preferably about 1 to about 4 quivalents, of an acid 23 are added to dissolve the TAT; as a result, a soluble salt of TAT is formed, herein referred to as "TAT salt." Any acid which allows for the dissolution of TAT in water and its subsequent re-precipitation is suitable. The selection of the acid depends on the specific needs and is based on solubility data and is easily done by one skilled in the art. Examples of suitable acids include without limitation HCl, acetic acid, $H_2SO_4$, and $H_3PO_4$. HCl is preferred, and the TAT salt generally prepared is TAT.4HCl. The solution may be heated to facilitate dissolution. Optionally, a co-solvent may be present. Examples of co-solvents include without limitation methanol, ethanol, and isopropanol. Optionally, the solution may be filtered through an absorbent material capable of absorbing impurities. Examples of absorbent materials include without limitation active carbon, alumina and microporous styrene.

The resulting reaction mixture 24 is then filtered 25, typically at a temperature in the range of about 60° C. to about 80° C., to remove the spent hydrogenation catalyst 26, preferably by passing through a carbon filter bed. The spent catalyst can then be recycled.

The filtered reaction mixture (or "filtrate") is a TAT salt solution and can be treated in either of two ways. To make TAT directly, a base (e.g., sodium hydroxide) is added to the filtrate.

Alternatively, as in the embodiment shown in FIG. 1, acid is added 28 at a temperature in the range of about 10° C. to about 80° C. to form and precipitate the TAT salt 27, for example, TAT.4HCl. Examples of suitable acids include without limitation HCl, acetic acid, $H_2SO_4$, and $H_3PO_4$. HCl is preferred. The amount of acid needed for this step will depend on the concentration of TAT in the filtrate and is readily determined by one skilled in the art. Typically, about 6 to about 8 equivalents of acid (as for example, 38% $HCl_{aq}$) are needed in this step to precipitate the TAT salt (for example, as TAT.4HCl) in about 90% yield. The use of gaseous acid, such as gaseous HCl, might reduce the total volume of liquid needed since the additional introduction of water with aqueous acid in both addition steps increases the absolute solubility of the TAT salt in the filtered reaction mixture. The addition of equivalent amounts of acid in the gas phase instead of as an aqueous solution (for example, $HCl_{gas}$ instead of $HCl_{aq}$) is preferred since the liquid volumes are thereby reduced, and crystallization yields are expected to be higher as a consequence. Aqueous acid (for example, 30-38 wt % HCl) may be used because it is easier to handle than the acid in the gas phase. Aqueous acid can be recovered 29, distilled 30, and recycled (30, 28) or used in the acid wash step of the process (30, 33, 44).

To facilitate the precipitation of the TAT salt (for example, as TAT.4HCl) an aliphatic alcohol co-solvent may optionally be added. Examples of suitable alcohol co-solvents included without limitation: methanol, ethanol, n-propanol, and isopropanol.

A small amount of tin (e.g., about 0.5% tin powder) is optionally added 37 to reduce impurities caused by oxidation and to prevent further impurity formation by that route.

The reaction mixture containing the precipitated TAT salt is then cooled to about 5° C. to about 15° C. and stirred, then filtered. The TAT salt is then washed 44. It may be washed with deaerated aqueous acid, such as HCl (33%), and then optionally with deaerated ethanol or methanol to produce a wet cake material. The used acid can then be distilled and recycled (31, 30, 33). The optional ethanol or methanol wash can be recycled as shown in FIG. 1 48, 47 and a purge is drawn to prevent accumulation. Using an agitated filter unit during the wash procedures can allow for a reduction of the wash volumes. Under such circumstances, using small amounts of cold (e.g., about 5° C.) water instead of the aqueous acid would be effective; cold water would be used because of lower solubility of the TAT salt in cold water versus, e.g., room temperature. For example, the solubility of TAT.4HCl in water at 25° C. is about 16 wt %.

Whether aqueous acid or cold water is used as a wash, it may be possible to eliminate the ethanol/methanol wash and dry directly from aqueous wet cake or simply use the wet cake in subsequent processing.

The resulting wet cake material (TAT salt) can be used in subsequent processing without drying or can be dried, as in FIG. 1 44, for example at a pressure less than 400 Torr and a temperature of about 30° C. to about 50° C., under a stream of $N_2$ 49. The dried product 50 is preferably kept under nitrogen.

The yield of TAT salt can be increased by recovered additional TAT salt from the filtrate remaining from the reaction mixture that contained the precipitated TAT salt (i.e., the "mother liquor") by, e.g., evaporation of water.

Oxygen is excluded throughout all steps of the process of making the TAT salt. Deaerated water and deaerated acid are used.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

Materials 2,6-diamino-3,5-dinitrotoluene, 98% pure, was made using the methods described for, 1,3-diamino-4,6-dinitrobenzene ("DADNB"), by making 1,3-dichloro-4,6-dinitrotoluene from 2,6-dichlorotoluene analogous to the method described in Knobloch et. al., Chem. Ber. 91, 2563 (1958) for making 1,3-dichloro-4,6-dinitrobenzene from 1,3-dichlorobenzene; and amination of the 1,3-dichloro-4,6-dinitrotoluene according to the method described in Boyer et. al., J. Am. Chem. Soc. 82, 2213 (1960).

Dry basis 5% Pt on C ("5% Pt/C") catalyst, wetted with 50% water, Degussa F101, was obtained from Degussa, now Evonik Degussa, a subsidiary of Evonik Industries AG, Essen, Germany.

The meaning of abbreviations is as follows: "DADNT" means 1,3-diamino-4,6-dinitrotoluene, "g" means gram(s), "gal" means gallon, "h" means hour(s), "L" means liter(s), "mL" means milliliter(s), "min" means minutes, "mol" means mole(s) or molar, "MPa" means megapascal(s), and "psi" means pounds per square inch.

Example 1

This Example demonstrates the preparation of TAT.4HCl salt in high yield. All operations were conducted under exclusion of oxygen.

A 1 gal (3.79 L) stirred Hastelloy autoclave was charged with 410 g of DADNT, and 8.3 g of 5% Pt/C The autoclave was purged 5 times with $N_2$ and 2 times with $H_2$ at 90 psi (0.62 MPa). Subsequently, 1200 mL of deaerated water (purged with $N_2$ overnight) was added and the mixture was pressurized at 81° C. to 300 psi (2.07 MPa). Hydrogenation was continued for a total time of 3 h with an approximate uptake of 6.5 mol equivalents of $H_2$. The excess hydrogen was released and the autoclave was cooled to 40° C. and purged twice with $N_2$, after which 915 g of deaerated $HCl_{aq}$ (34%, by titration) was added. The mixture was stirred and heated back up to 80° C., then passed through a carbon bed filter at 75° C. to remove catalyst and a small amount of unconverted starting material. The solution was directly charged into a stirred vessel and cooled to 40° C. Subsequently, 1000 mL of deaerated ethanol followed by 1000 mL of deaerated $HCl_{aq}$ (38%) were added over a time period of 15 min with vigorous stirring. The temperature was reduced to 5° C. and the white precipitate of TAT.4HCl formed. After completion of the precipitation, the salt was filtered through a glass frit and washed twice with 300 mL deaerated $HCl_{aq}$ (33%) and twice with 200 mL deaerated ethanol. The resulting wet cake material (white TAT.4HCl salt) was dried at a pressure under 400 Torr and a temperature of 30-50° C. under a stream of $N_2$, using a heating mantel around the filter unit set at 40° C. Vacuum was pulled at the bottom of the unit and a stream of $N_2$ was supplied to the top of the unit, maintaining a positive pressure above the filter.

The net yield was 542 g, 96% based on 98% pure 2-methyl-1,3-diamino-4,6-dinitrotoluene starting material.

The materials, methods, and examples herein are illustrative only and, except as specifically stated, are not intended to be limiting.

Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

What is claimed is:

1. A process for preparing 2,3,5,6-tetraaminotoluene

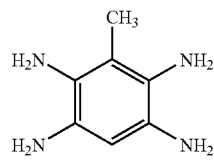

comprising contacting 2,6-diamino-3,5-dinitrotoluene (II)

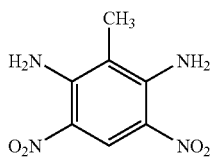

with a hydrogenation catalyst and hydrogen gas, in water in a reaction vessel, to form a reaction mixture, at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraaminotoluene (I); and subsequently filtering the reaction mixture, thereby removing the spent hydrogenation catalyst.

2. A process for preparing a 2,3,5,6-tetraaminotoluene salt comprising:

(a) contacting 2,3,5,6-tetraaminotoluene

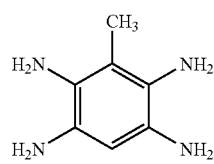

with an aqueous solution comprising 1 to 6 equivalents of acid per mol of 2,3,5,6-tetraaminotoluene, optionally heating the solution, thereby dissolving the 2,3,5,6-tetraaminotoluene;

(b) forming and precipitating the 2,3,5,6-tetraaminotoluene salt by adding an acid to the dissolved 2,3,5,6-tetraaminotoluene; and (c) washing the 2,3,5,6-tetraaminotoluene salt, wherein all steps are performed under oxygen exclusion.

3. The process of claim 2 wherein the 2,3,5,6-tetraaminotoluene in step (a) is prepared by contacting 2,6-diamino-3,5-dinitrotoluene (II)

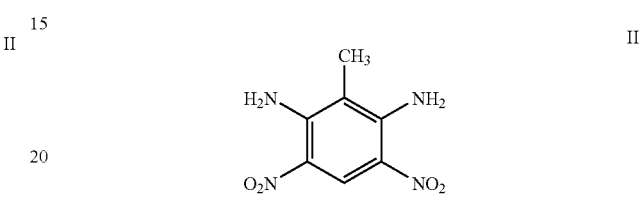

with a hydrogenation catalyst and hydrogen gas, in water in a reaction vessel, to form a reaction mixture, at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraaminotoluene (I); and subsequently filtering the reaction mixture, thereby removing the spent hydrogenation catalyst.

4. The process of claim 2 wherein the acid in steps (a) and (b) is selected from the group consisting of HCl, acetic acid, $H_2SO_4$, and $H_3PO_4$.

5. The process of claim 2 wherein the acid in step (b) is added in the gaseous state.

6. The process of claim 2 wherein the acid is added in step (b) in an amount of about 6 to about 8 equivalents.

7. The process of claim 2 further comprising drying the 2,3,5,6-tetraaminotoluene salt.

* * * * *